US010993858B2

(12) United States Patent
Lumaque-Steeman et al.

(10) Patent No.: US 10,993,858 B2
(45) Date of Patent: May 4, 2021

(54) URINE ABSORBENT PAD

(71) Applicant: EZ Male Pads, Inc., Long Beach, CA (US)

(72) Inventors: Lorna Mateo Lumaque-Steeman, Moreno Valley, CA (US); Wade C. Johnson, Long Beach, CA (US)

(73) Assignee: EZ MALE PADS, INCORPORATED, Long Beach, CA (US)

( * ) Notice: Subject to any disclaimer, the term of this patent is extended or adjusted under 35 U.S.C. 154(b) by 1016 days.

(21) Appl. No.: 15/087,557

(22) Filed: Mar. 31, 2016

(65) Prior Publication Data

US 2016/0278991 A1 Sep. 29, 2016

Related U.S. Application Data

(63) Continuation-in-part of application No. 14/673,549, filed on Mar. 30, 2015, now Pat. No. 10,588,793.

(60) Provisional application No. 61/998,947, filed on Jul. 14, 2014.

(51) Int. Cl.
*A61F 13/58* (2006.01)
*A61F 13/56* (2006.01)
*A61F 13/471* (2006.01)
*A61F 13/15* (2006.01)

(52) U.S. Cl.
CPC ............ *A61F 13/58* (2013.01); *A61F 13/471* (2013.01); *A61F 13/5616* (2013.01); *A61F 2013/15146* (2013.01); *A61F 2013/583* (2013.01)

(58) Field of Classification Search
CPC ................................. A61F 13/45; A61F 13/58
See application file for complete search history.

(56) References Cited

U.S. PATENT DOCUMENTS

| 4,216,773 | A | | 8/1980 | Ryan | |
|---|---|---|---|---|---|
| 6,129,719 | A | * | 10/2000 | Nozaki | ................. A61F 13/471 604/385.01 |
| 6,443,934 | B1 | | 9/2002 | Glaug et al. | |
| 2006/0282055 | A1 | | 12/2006 | Shiomi et al. | |
| 2012/0197228 | A1 | | 8/2012 | Miyake et al. | |
| 2016/0008188 | A1 | * | 1/2016 | Lumaque-Steeman | ..................... A61F 13/5616 604/385.04 |

FOREIGN PATENT DOCUMENTS

JP H0938127 A 2/1997

OTHER PUBLICATIONS

International Search Report for PCT/US2017/025121 filed Mar. 30, 2017.
International Search Report dated Aug. 28, 2015 as issued by the International Search Authority (ISA/US) for related PCT international application PCT/US2015/030857 with IFD of May 13, 2015.

* cited by examiner

*Primary Examiner* — Benjamin J Klein
(74) *Attorney, Agent, or Firm* — Fulwider Patton LLP

(57) ABSTRACT

A disposable urine trap in the form of a foldable pad that envelops the male genitalia and closes around the organ to form a barrier that prevents urine from escaping the trap. The pad includes an asymmetric pair of wings that are separated by a gap and attached to the main body of the pad. The first wing is preferably trapezoidal and a second wing having an extending distal edge.

8 Claims, 23 Drawing Sheets

URINE ABSORBENT PAD

CROSS-REFERENCES TO RELATED APPLICATIONS

This application is a continuation-in-part of U.S. patent application Ser. No. 14/673,549 filed Mar. 30, 2015, which claims priority from U.S. Provisional Patent Application No. 61/998,947, filed Jul. 14, 2014, the contents of both of which are incorporated by reference herein in their entirety.

BACKGROUND

The present invention relates generally to adult incontinence, and more particularly to a urine absorbent pad designed for a male that provides an easy and convenient manner to more safely replace soiled protective wear than the prior art.

Urinary incontinence (UI) is defined as the involuntary loss of urine. In both men and women, age is a consistently reported risk factor for UI; however, it is not considered a normal consequence of aging. Overall, UI affects up to 30% of community dwelling older adults and more than 50% of nursing home residents. Despite its high prevalence, up to one-half of cases may not be reported because individuals with UI may not seek medical intervention. Embarrassment and the perception that UI is an expected consequence of aging are common factors in the failure to seek a solution or treatment. That reluctance is particularly strong in men, who often deem the problem to be associated with a loss of masculinity.

Urinary incontinence is categorized according to pathophysiology and clinical presentation. The four main categories are (1) stress urinary incontinence (SUI), (2) urge urinary incontinence (UUI), (3) overflow incontinence, and (4) functional incontinence. Mixed types of incontinence are common and may complicate diagnosis and treatment because of overlapping symptoms. Studies have found that UI significantly affects psychological well-being and health care-related quality of life. Urinary incontinence may impair sexual function, restrict activities, interfere with interpersonal relationships, decrease self-esteem, increase caregiver burden, increase financial burden, and cause anxiety or depression. It is a common precipitant of institutionalization in older adults.

Because of current demographic trends, UI is an increasingly common medical and socioeconomic problem. One place where the issue arises with great propensity is nursing homes, where older patients often suffer moderate to severe UI due to a variety of physiological conditions. In men, incontinence is often related to prostate problems or treatments that become exacerbated in the elderly. Certain medical conditions, particularly those affecting the brain or nervous system, such as Alzheimer's, Parkinson's, Dementia, Multiple Sclerosis and brain damage, can also lead to incontinence. This is due to the nerve passageways from the brain becoming damaged. The result can be either an overactive bladder (the need to go often and frequently) or an under-active bladder (ineffective emptying leading to leakage). Diabetes and or a stroke can also bring on incontinence.

With aging, bladder capacity decreases, ability to inhibit urination declines, involuntary bladder contractions (detrusor overactivity) occur more often, and bladder contractility is impaired. Thus, voiding becomes more difficult to postpone and tends to be incomplete. Postvoid residual volume increases in as much as ≤100 mL (normal <50 mL). A weakening of the endopelvic fascia often results as well. In men, the tendency for the prostate to enlarge with age causes the partial obstruction of the urethra, leading to incomplete bladder emptying and strain on the detrusor muscle. These changes occur in many normal, continent elderly males and may facilitate incontinence but do not cause it.

One challenge associated with male incontinence is the necessity for changing clothing, bedding, and other items that may become soiled due to an incontinence patient. When a disabled patient has voided his urine, the caregiver(s) must remove the patient's clothing and bedding while the patient is in a prone position. This can be challenging to the caregiver(s), who must lift the patient to remove the clothing and bedding while simultaneously trying to extract the soiled garments and sheets, blankets, etc. If the patient is large or overweight, the problem becomes magnified even greater. The task is thus labor intensive and time consuming, and can result in injury to the care giver(s) from reaching over the bed in an awkward position to hoist the patient, particularly when multiplied by changes every five or six hours, or in the case of facilities offering extraordinary care, every two hours or so. Additionally, adult diapers are typically relatively large and bulky to cover the patient's groin and anal area, thus adding to the bulk for supply and disposal of some four to ten diapers a day.

Elderly patients and residents of nursing homes who are immobile or have reduced mobility are at high risk for developing pressure ulcers (bed sores). This condition is exacerbated if the patient is incontinent because the moisture from urine causes the surface of the skin to become irritated and infected. For this reason, it is important to prevent urine from migrating to extended areas of the skin and from remaining in contact with any part of the skin for any extended period of time, and that it be removed as soon as possible.

The U.S. Census Bureau estimates there are 76.4 million baby boomers, and the oldest of this generation, which includes those born between 1946 and 1964, are over 65 years old. For many of these people, adult diapers are a way to ameliorate the effects of moderate to severe incontinence. Adult diapers are a $7 billion global market, and sales have grown more than 8 percent over the past five years due to this increasing number of baby boomers entering their 70s and 80s. This trend appears to be rising as the stigma of wearing protective undergarments becomes less and the popularity of these products grow.

Frequently two or more caregivers will be assigned to the changing task each time the diaper is soiled. The task itself can be quite time consuming, particularly if fecal matter has migrated from the anal area due to defecation and propagated by urine saturated in an outer diaper.

For males, particularly invalid males, diapers can be an unsatisfactory solution for several reasons. First, the previously raised issue that, once soiled, the patient must be changed like an infant by a caregiver who may not have the strength to lift a full grown adult male. Changing a diaper can lead to the patient being moved in positions that may strain or injure the patient, particularly when moved by a caregiver with inadequate strength to properly maneuver a full grown adult male. Second, unlike females where the origin and direction of the urine stream is fairly predictable, males tend to urinate from different positions, angles, and directions, and this inconsistency leads to leakage. This is especially true when the patient is lying on his back and suffers incontinence, because a gap in the top of the diaper at the patient's stomach can provide an opening where urine can leak outside of the diaper, leading to the issues raised above. Patients who go frequently can get ignored because of the challenges in changing the patient, leading to health issues as well.

Efforts have been made to devise an absorbent pad to cover the penis. One such device is in the form of an elongated rectangular pad foldable along a centrally transverse fold line and configured on one end with a U-shaped opening to receive a penis to be positioned between the two halves. A device of this type is shown in U.S. Pat. No. 6,129,719 to Nozaki. Such devices, while effective to absorb some of the urine released, suffer the shortcoming that the device is relatively bulky, is inconvenient to apply and fails to securely entrap the penis to protect against release of urine outside the pad.

The art is in need of a simple, cost effective device that is directed to the problem of male incontinence, and can reduce the opportunity for leakage as well as the frequency and extent to which a patient must be moved for a change after an incontinent event has occurred. The present invention is directed to this objective.

SUMMARY OF THE INVENTION

In one aspect, the present invention is directed to a disposable urine trap in the form of a foldable pad that envelops the male genitalia and closes around the penis to form a barrier to prevent urine from escaping the trap. The pad includes an asymmetric pair of wings that are separated by a void attached to the main body of the pad. The first wing is preferably rectangular in that the distal angles are substantially right angles with parallel side edges and a perpendicular distal edge, and has a length that exceeds a length of a second wing, which is terminates so that the distal edge of the second wing is angled to form an obtuse and an acute angle with respect to its generally parallel sides. The void between the two wings may be formed by eliminating a triangular component from each inner side of the first and second wings to establish a "kite" or "diamond"-shaped void in the pad. The void in the pad may receive the patient's penis at its base such that the penis extends over the widest and thickest portion of the pad and the head of the penis occupies the middle area of the pad. Once the pad is arranged so that the penis is laid over the pad through the void, the first wing is folded over the top of the penis along a crease where the void lies to overlay the penis and sandwich the penis between the pad and the first wing. The angle that the first wing protrudes away from the pad is selected so that the inner side edge of the first wing aligns with a proximal edge of the second wing when folded over penis as described above. The folding of the first wing closes the void so that the void now encircles the base of the penis as the penis lays on the pad. Once the inner side edge of the first wing is placed against the proximal edge of the second wing, the second wing is then folded over the first wing such that the distal edge of the first wing and the distal edge of the second wing are substantially orthogonal. The asymmetric nature of the first and second wings allow the configuration described above, such that the wings cooperate to overlay the penis can capture the penis between the two wings and the thick portion of the pad. An adhesive strip on the opposite side of the first wing attaches to the second wing and secures the urine trap in the closed configuration. The corners of the pad can then be folded over the outer side edges of the adjacent first and second wings to close the trap and envelope the penis inside the pad.

In another aspect, the urine trap is formed with a larger main absorbent region and distally projecting, flanking, first and second absorbent wings to be folded cooperating to form therebetween a gap terminating in a closed extremity defining an opening. The first wing is constructed to be folded proximally and laterally inwardly preferably over the main absorbent region to cover a wearer's penis projecting through the opening and overlapping the main absorbent region. The second wing is constructed to be folded proximally and laterally inwardly over such first wing to cooperate therewith in trapping the penis between the first wing and main absorbent region.

In a still further aspect, the main absorbent region is formed with a rounded proximal edge of a predetermined contour and the first wing is constructed with a distal edge formed with a complementary predetermined contour such that, when folded on the main region, the contours may be aligned.

In another aspect, the urine trap is formed with a large main absorbent region and distally projecting, flanking first and second absorbent wings cooperating to form therebetween a gap terminating in a closed extremity defining an opening. The first wing is constructed to be folded proximally and laterally inwardly over the main absorbent region to have a wearer's penis projecting through the opening and overlapping the main absorbent region. The second wing is constructed to be folded A benefit of the present invention is that it can be placed inside an undergarment such as an over-diaper. If a male patient should urinate in the urine trap with the patient on his back, a caregiver can simply remove the urine trap from the diaper or undergarment without the need to undress, change the over-diaper, or move the patient. A new urine trap can be placed on the patient with little or no disturbance to the patient and without rolling the patient over, lifting the patient, or undressing the patient. Moreover, the configuration of the urine trap minimizes any opportunity for leakage at the patient's waistline where most diapers can leak for male wearers. The way the wings of the present invention fold diagonally over one another to envelope the penis and isolate it and incoming urine from the abdomen, eliminating any gaps and serves to simplify changing and protect the patient's skin.

DETAILED DESCRIPTION OF THE PREFERRED EMBODIMENTS

Figure 1:
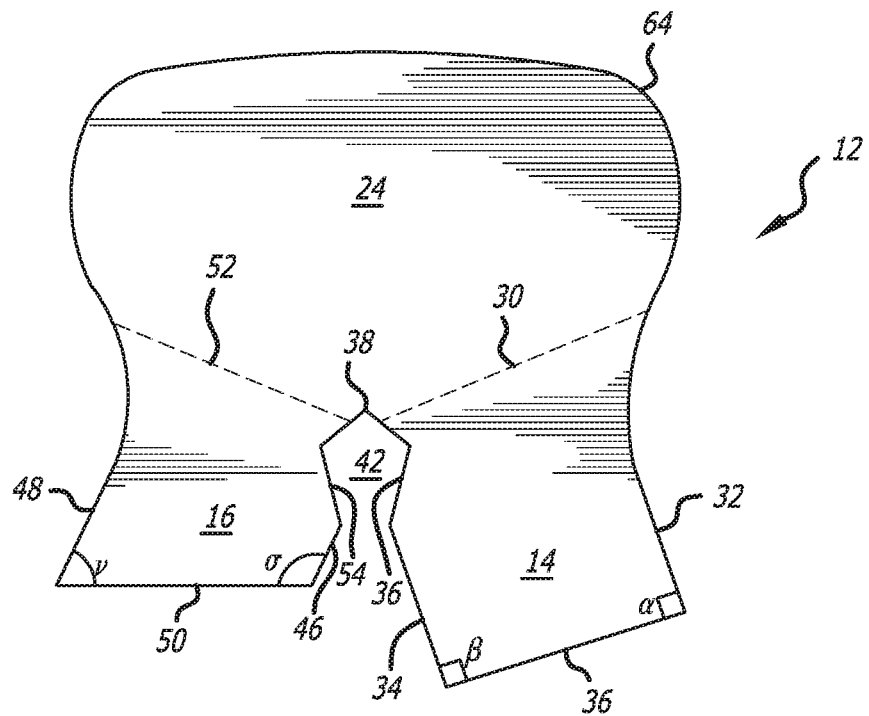
FIG. 1 is a top view of a first preferred embodiment of the present invention.

FIG. 1 illustrates a plan view of a first preferred embodiment of the present invention, comprising a pad 12 generally formed by a base 24 and first and second wings 14, 16. The pad 12 is formed by enclosing fluid absorbent material between an fluid impervious outer lining 18 and a soft fluid transmissive inner lining 20. The outer lining 18 may be made of a polyethylene film or other low cost, biocompatible material to seal in the urine and prevent leakage outside of the trap. The inner lining 20 that bear's against the user's skin may be made of polypropylene or suitable non-abrasive, non-toxic material that transmits fluid while largely staying relatively fluid free at the surface. The absorbent center 22 may contain wood pulp and super-absorbent polymers such as sodium polyacrylate. Sodium polyacrylate is effective in wicking away fluid from the skin through the inner lining 20, and can soak up to 30 times its weight in urine. The absorbent center is bordered around its edges by adhering the inner lining 20 and outer lining 18, and the matching of the two mating linings 18,20 can be arranged to give the pad a rounded shape 64 in the undeformed condition. That is, a shallow, conically shaped "bowl" or saucer is created by the fit of the two mating edges such that the edges of the pad are raised with respect to the base 24. The main region of base 24 is particularly padded at this middle portion, which is where the introduction of urine is expected in most cases.

As further seen in FIG. 1, the first wing 14 extends outwardly from an imaginary fold line 30. The first wing 14 includes an outer side edge 32, an inner side edge 34, and a distal edge 36. The side edges 32,34 are substantially parallel, and the distal edge substantially perpendicular thereto, such that right angles α, β are formed. A generally triangular portion 36 of the inner edge 34 is removed at the juncture 38 of the first and second wings 14, 16, creating half of a void 42 through which the penis 76 is inserted.

The second wing 16, which in a preferred embodiment has a length that is approximately one half a length of the first wing 14, protrudes from an imaginary fold line 52 and includes an inner side edge 46, outer side edge 48, and distal edge 50. As with the first wing, the inner side edge 46 and outer side edge 48 are substantially parallel, but the distal edge 50 forms an acute angle ν with the outer side edge 48 and an obtuse angle σ with the inner side edge 46. A triangular portion 54 of the inner edge 46 is removed at the juncture 38 of the first and second wings 14, 16, creating the other half of the void 42, which is thusly formed in a shape of a diamond based on the two triangular resections 36,54 on the inner edges 34, 46.

Figure 2:
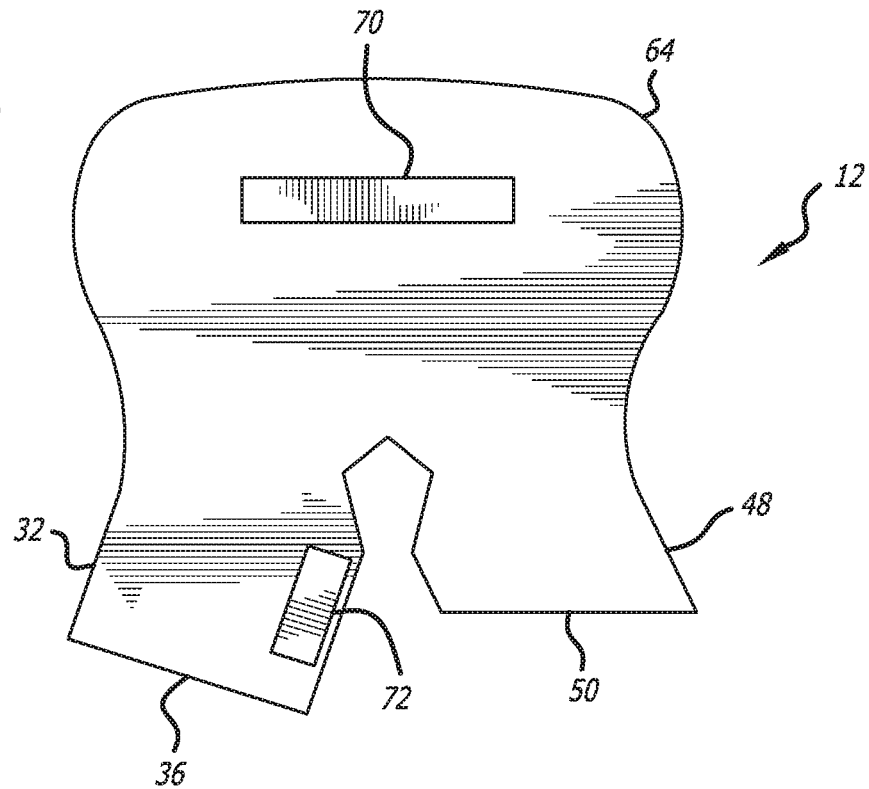
FIG. 2 is a bottom view of a the embodiment of FIG. 1.
Figure 3:
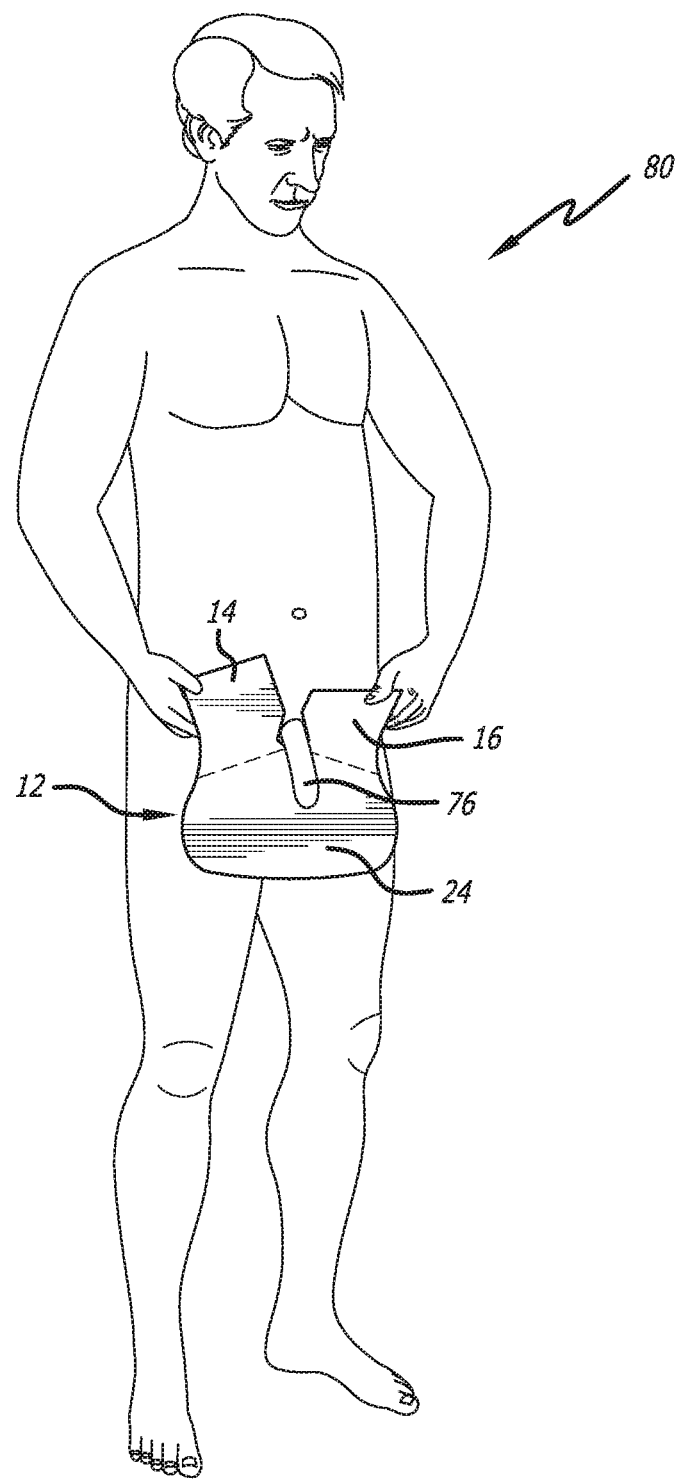
FIG. 3 is an elevated, perspective view of the present invention shown on a male user.

FIG. 2 illustrates a rear view of the pad 12, including a peel away adhesive strip 70 that can be used to secure the pad to the patient or a waistband of the patient. A second adhesive strip 72 is used to hold the pad in a pouch, or folded position to envelope the patient's genitalia 76.

Figure 4:
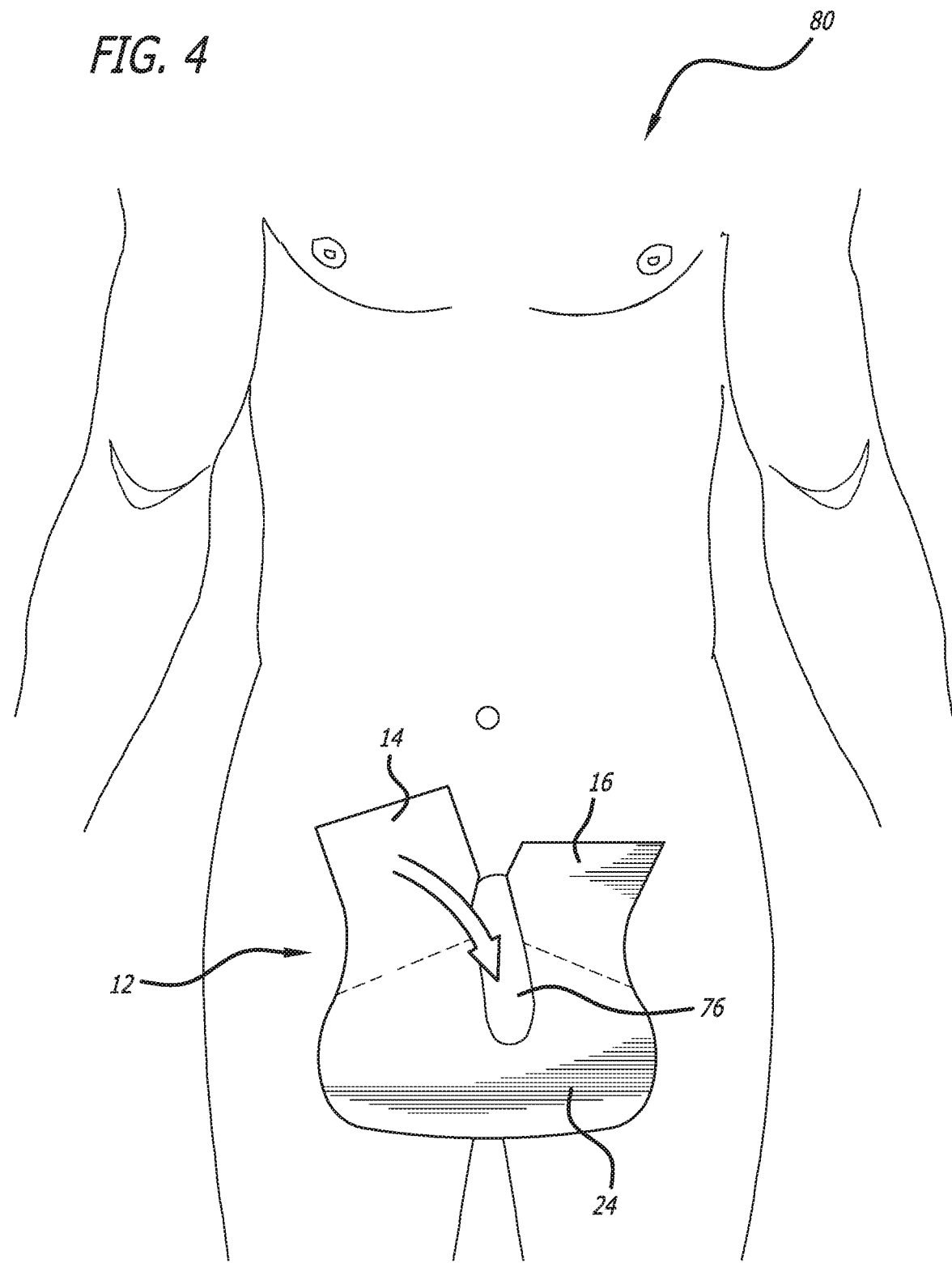
FIG. 4 is an enlarged, perspective view of the present invention.
Figure 5:
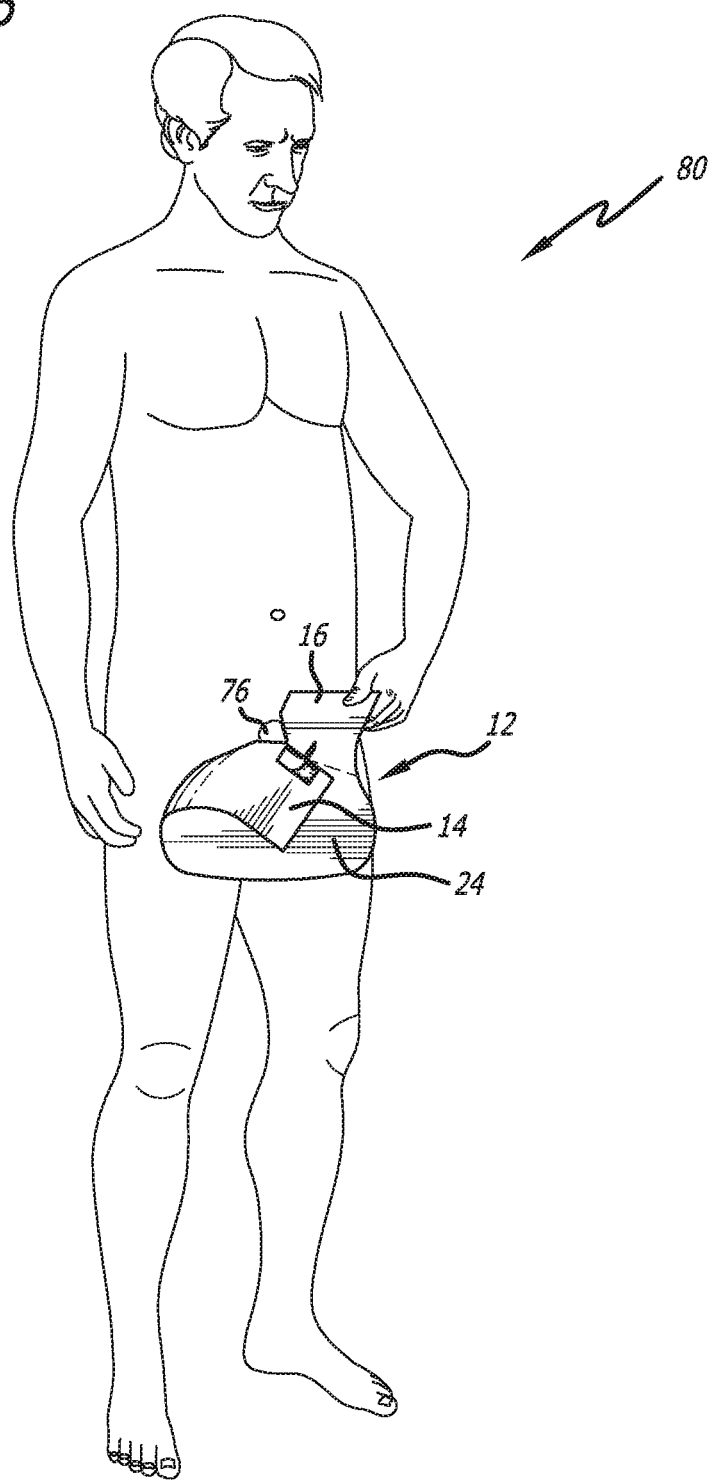
FIG. 5 is an elevated, perspective view of the present invention with the first wing folded.
Figure 6:
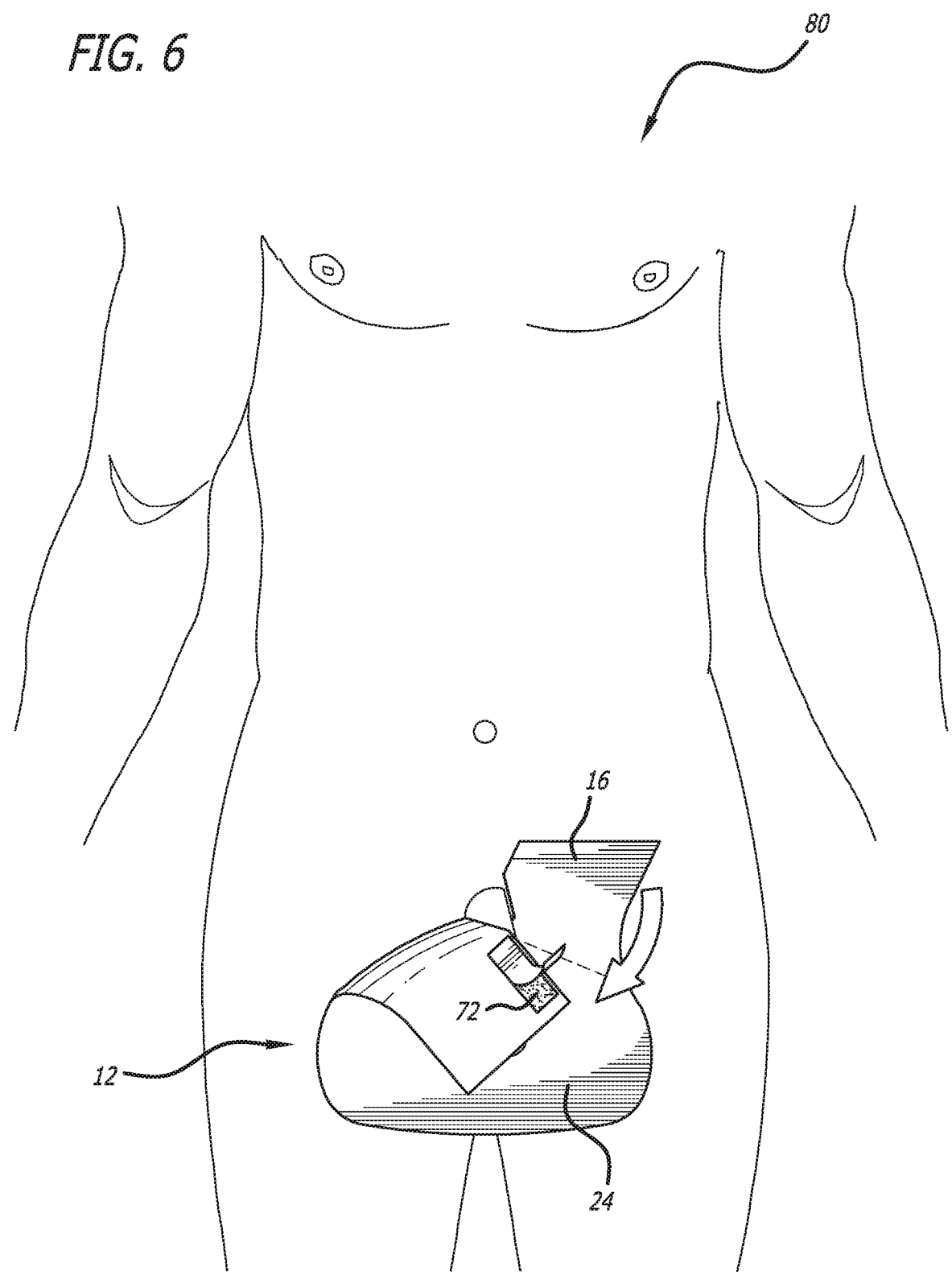
FIG. 6 is an enlarged, perspective view of the present invention with the adhesive strip removed.
Figure 7:
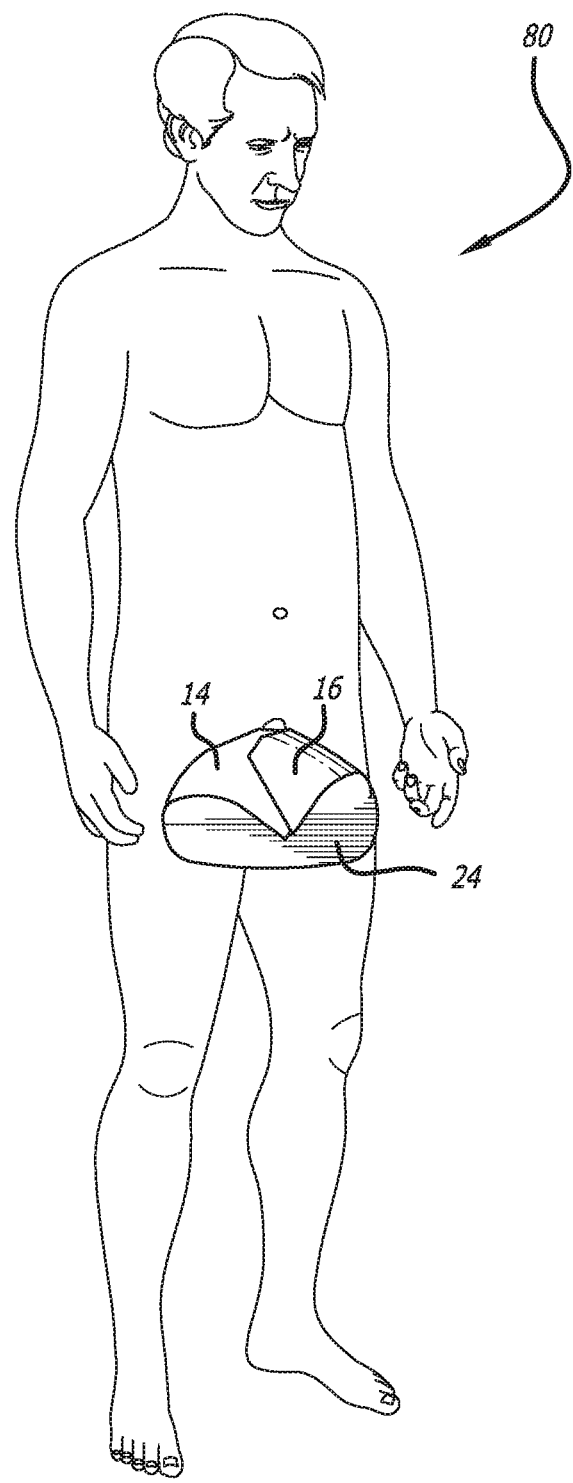
FIG. 7 is a perspective view of the second wing folded into place.
Figure 8:
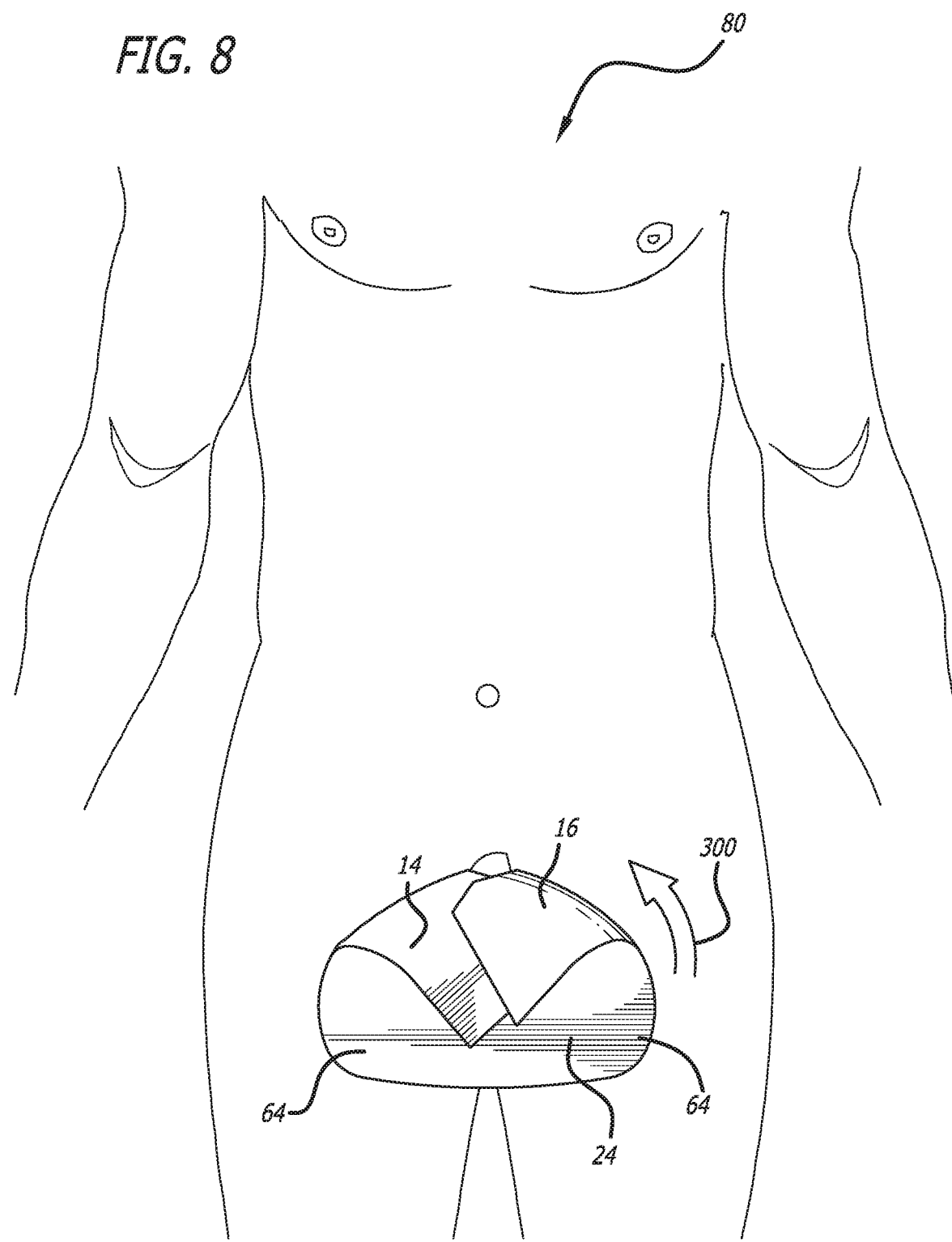
FIG. 8 is an enlarged, perspective view of corners being upturned to enclose the male genitalia.

FIGS. 3-13 illustrate a first method for how the pad 12 encloses the male organ and creates a cocoon-like wrap around the organ to collect any urine and prevent leakage. With the patient 80 preferably standing or lying on his back, the pad 12 is placed on the user's thighs with the first wing 14 on the upper right thigh/abdomen and the second wing 16 over the user's left thigh/abdomen. The user's penis 76 is placed in the void 42 between the first and second wings 14,16 so that the base of the penis is at the juncture 38 and the head of the penis is on the main region, or base 24 of the pad 12 (FIG. 4). The first wing 14 is then folded inwardly diagonally along the fold line 30 over the top of the penis such that the inner side edge 34 is approximately along fold line 52 (FIGS. 4, 5). The placement of the first wing 14 in this position covers the penis 76, and exposes the adhesive strip 72 adjacent the second wing 16. The protective cover is removed from the adhesive strip 72 (FIG. 6), and the second wing 16 is then folded at fold line 52 over the first wing 14 such that the distal edge 50 is approximately parallel to and adjacent to the side outer edge 32 of the first wing 14 (FIG. 7). This configuration encloses the penis 76 in the void 42 and creates a leak-proof pouch over the penis. The first and second wings 14, 16 overlap diagonally and cooperate to form a "V" shape over the penis (FIG. 8), angling diagonally toward the respective opposite corner 64 in the direction of arrow 300 (FIG. 8) to close the pouch like an envelope, eliminating any opportunity for urine to escape during urination. A double layer of protection created by the wings 14, 16 (FIGS. 12 and 13) reduces the opportunity for leakage and creates a drier, more moisture-free environment for the user 80.

Figure 9:
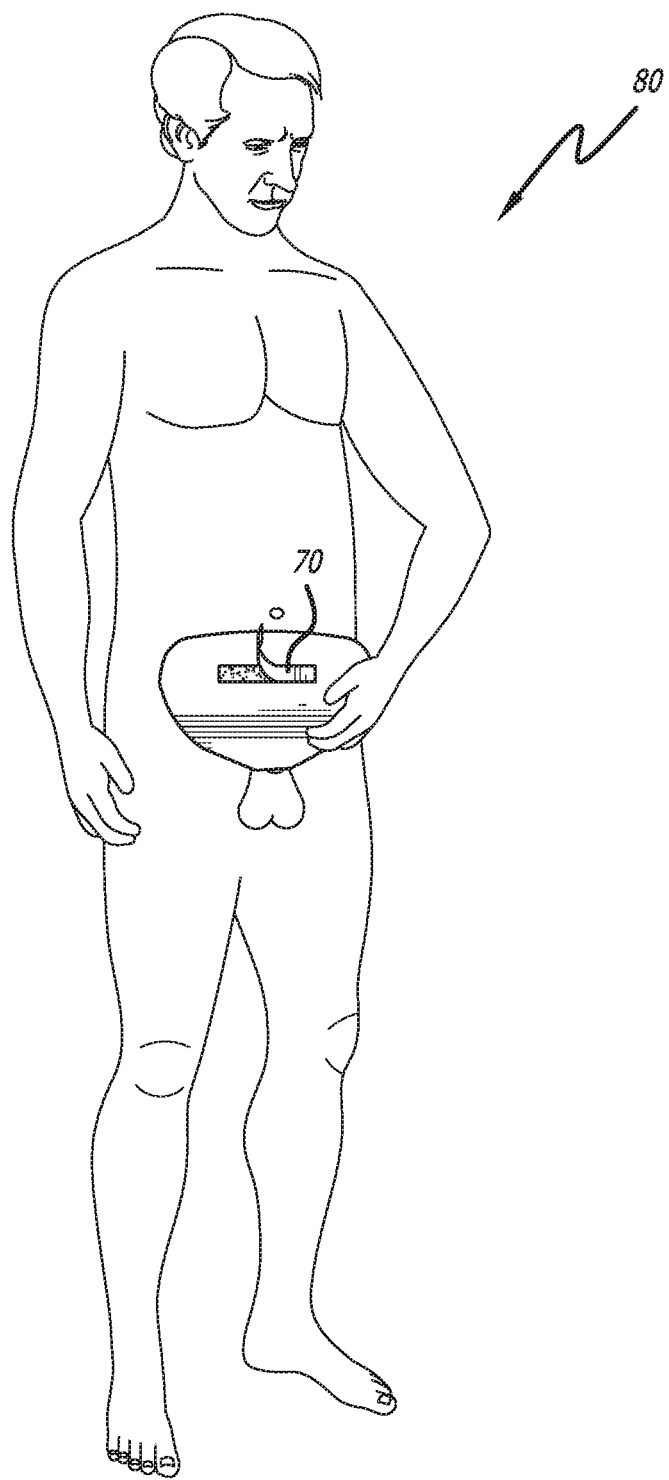
FIG. 9 is an elevated, perspective view of the adhesive strip being removed so as to be applied to a garment.
Figure 10:
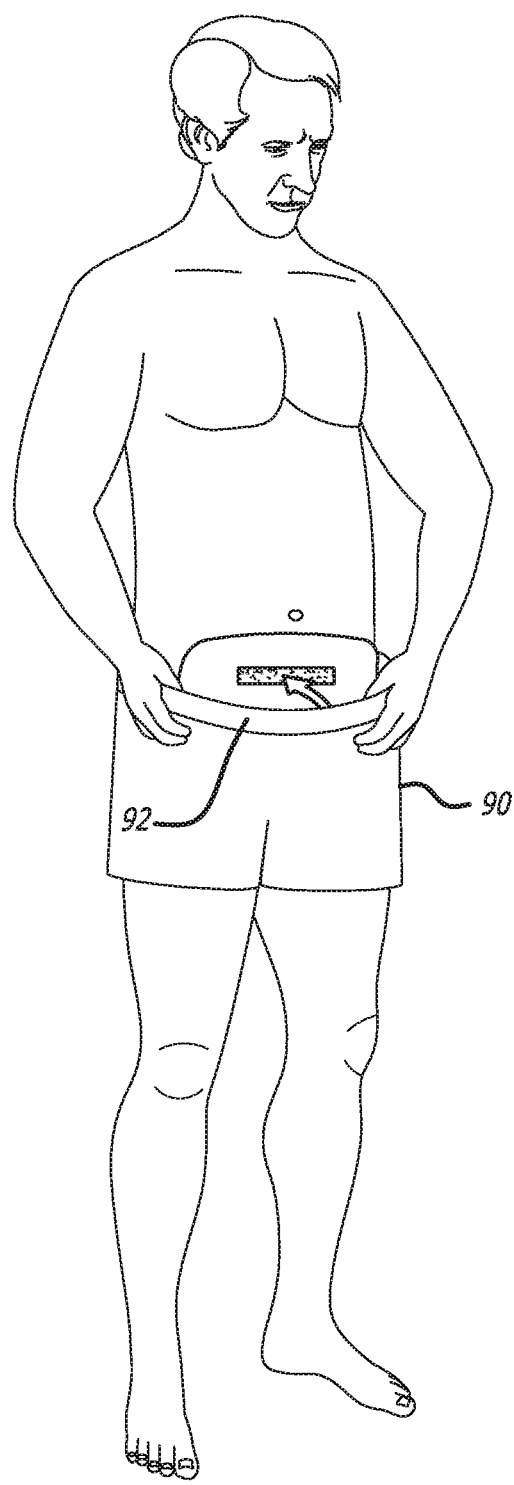
FIG. 10 is an elevated, perspective view of the pouch adhered to an undergarment.
Figure 11:
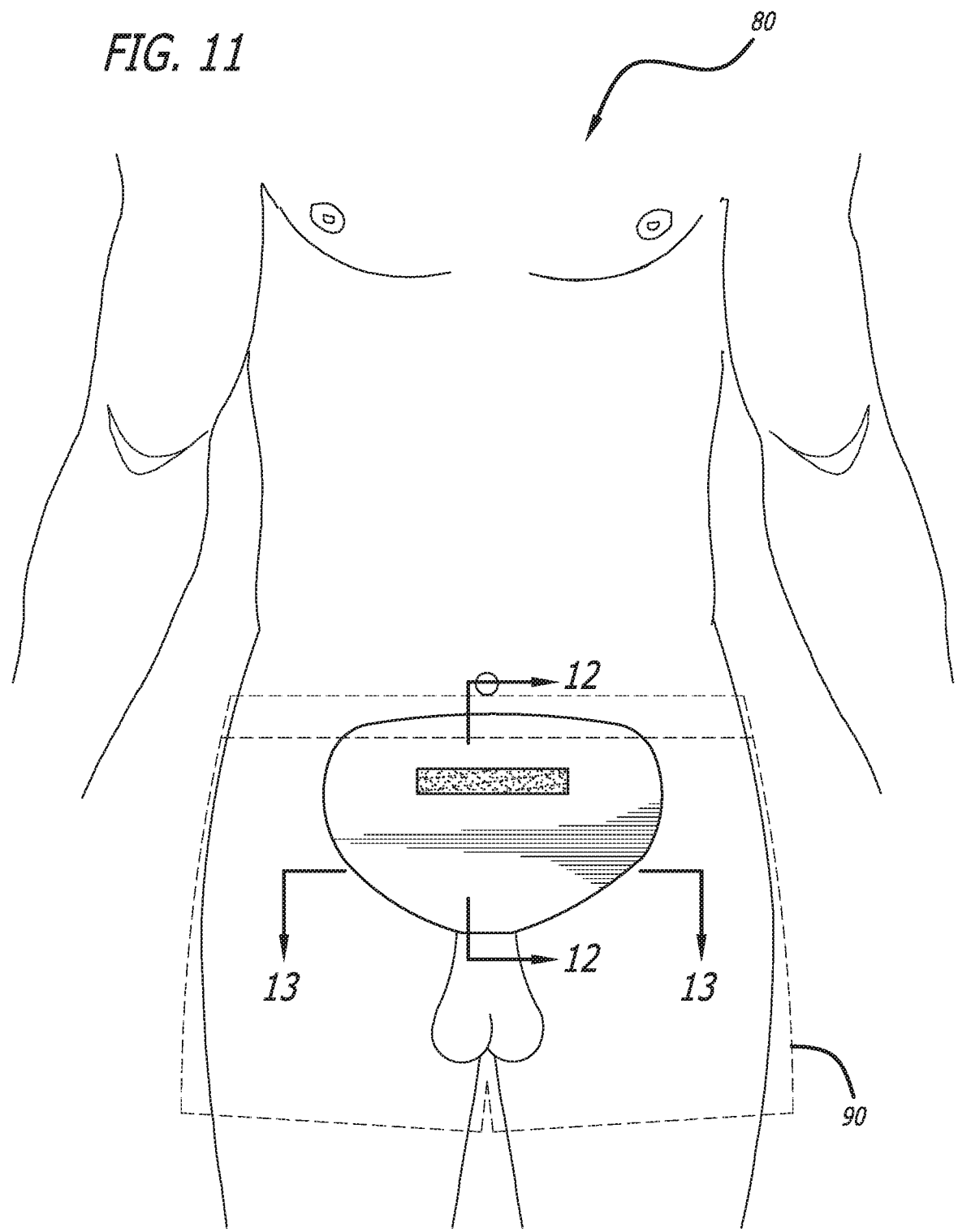
FIG. 11 is an enlarged, perspective view partially in shadow showing the pouch in place inside an undergarment.
Figure 12:
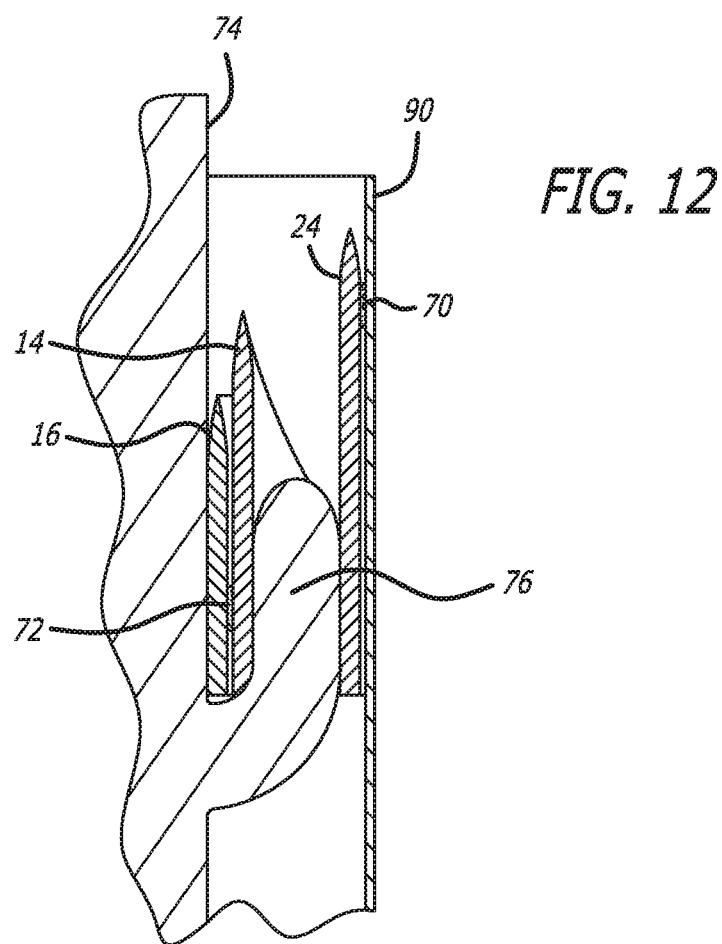
FIG. 12 is a first cross sectional view of the pad in the pouch configuration.
Figure 13:
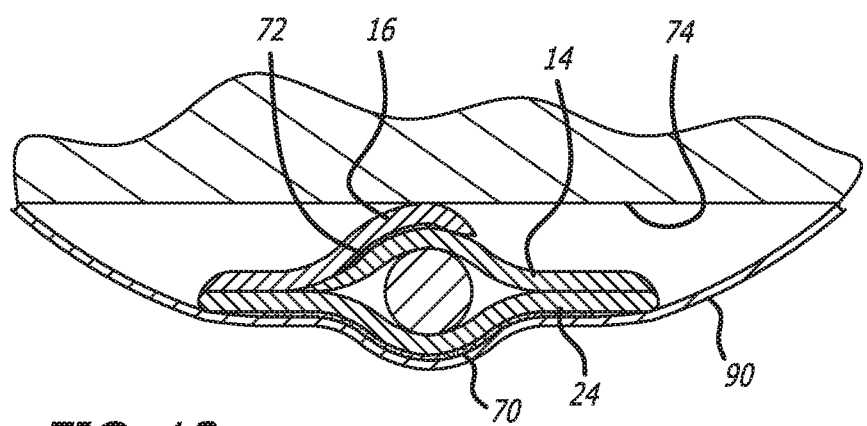
FIG. 13 is a second cross sectional view of the pad in the pouch configuration.
Figure 14:
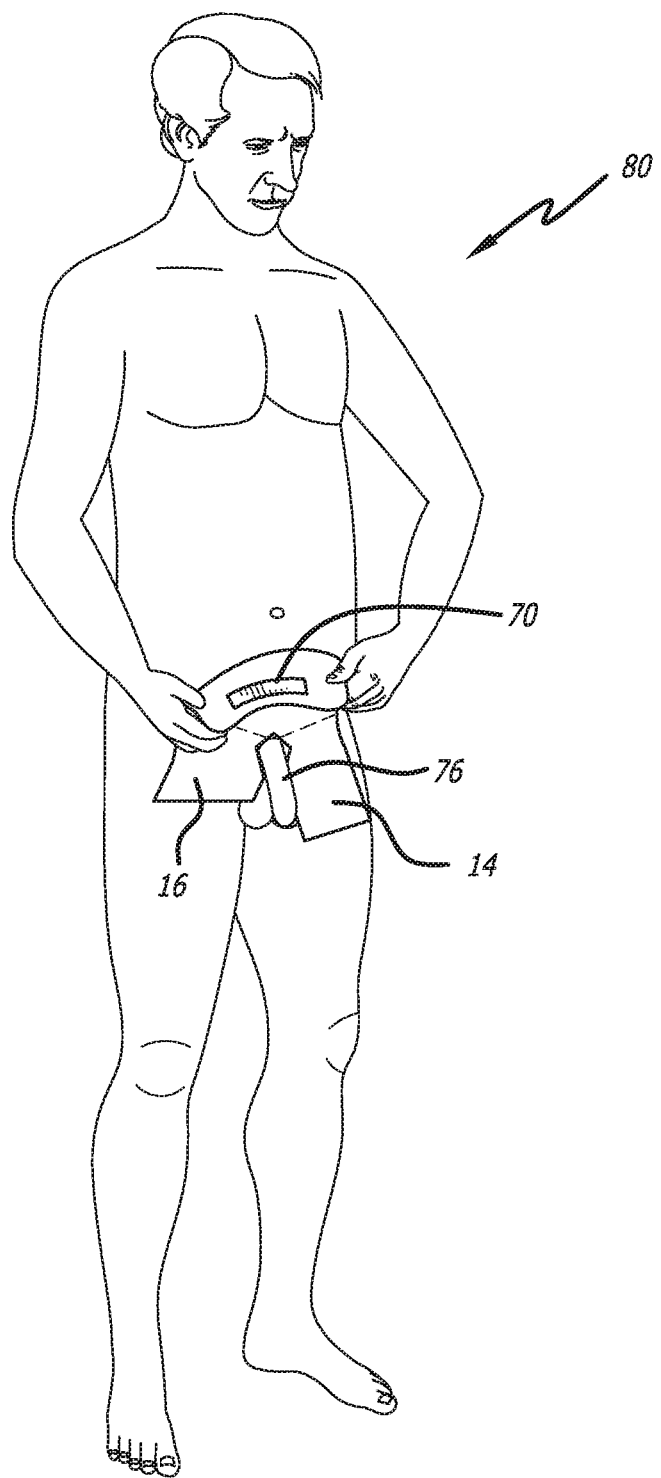
FIGS. 14-23 illustrate an alternate way of wearing the pad of the present invention.
Figure 15:
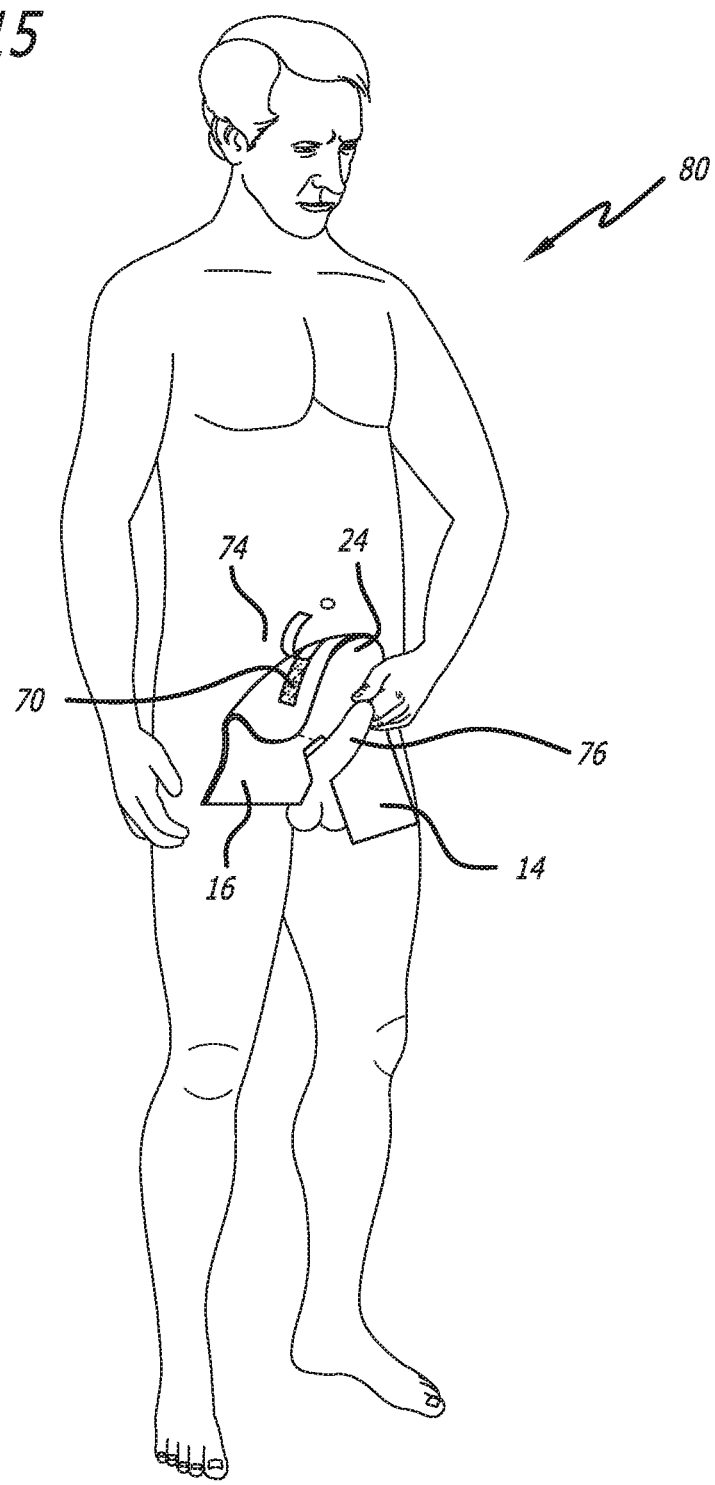
Figure 16:
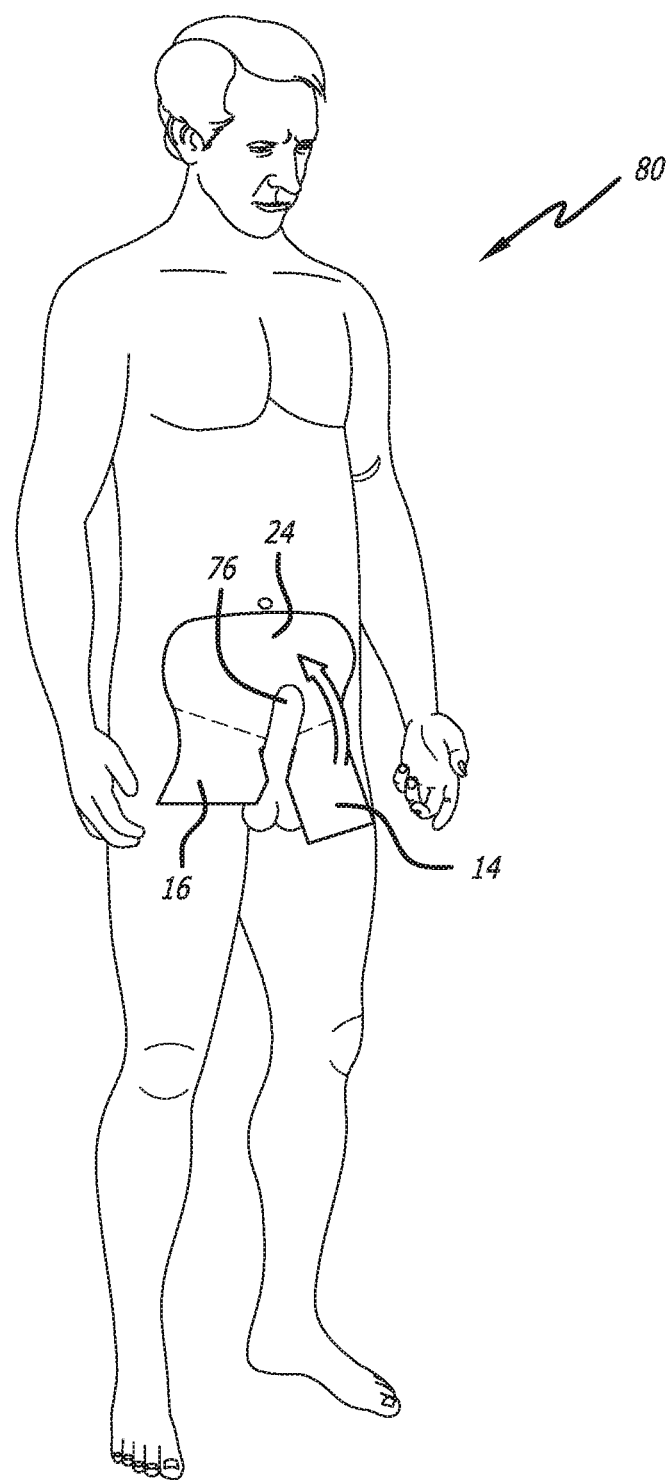
Figure 17:
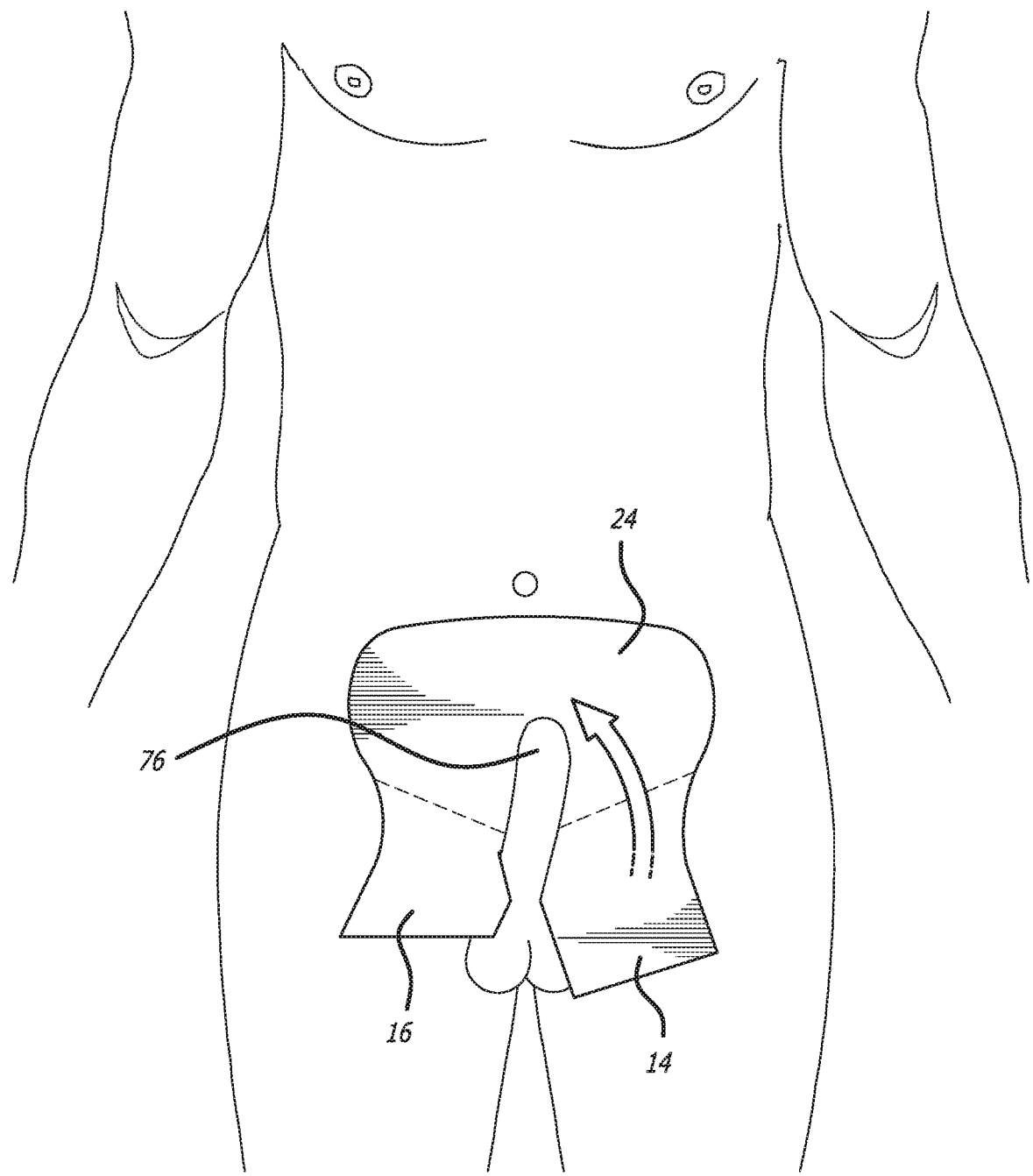
Figure 18:
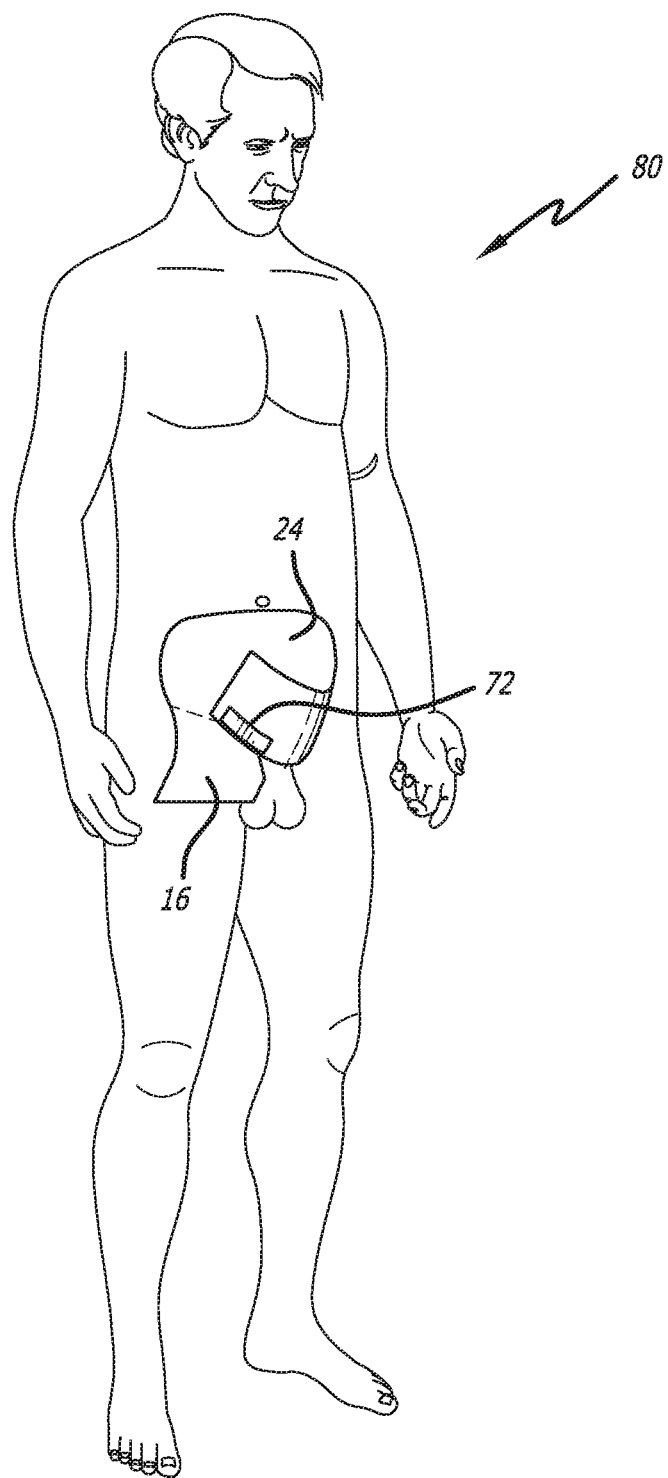
Figure 19:
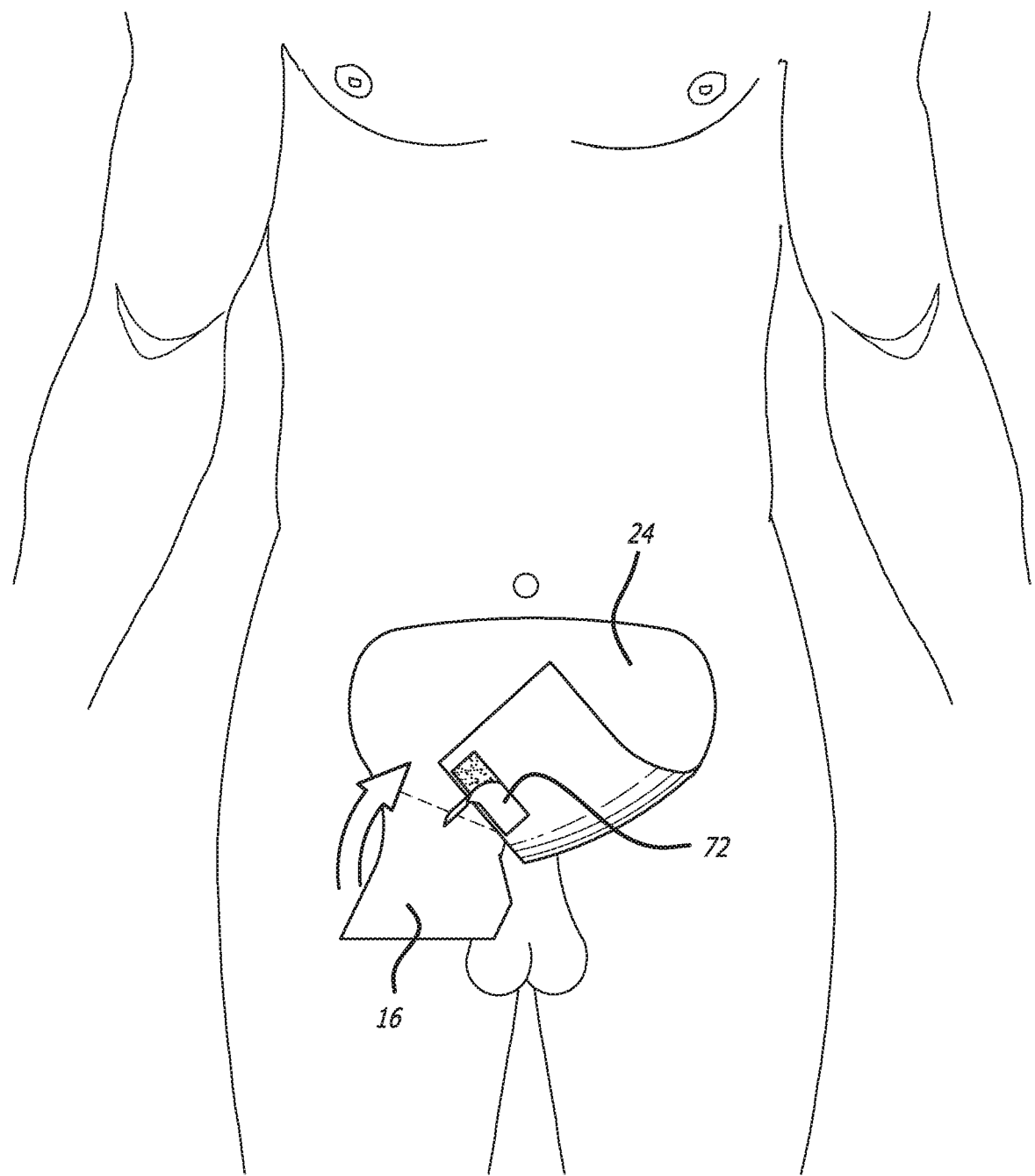
Figure 20:
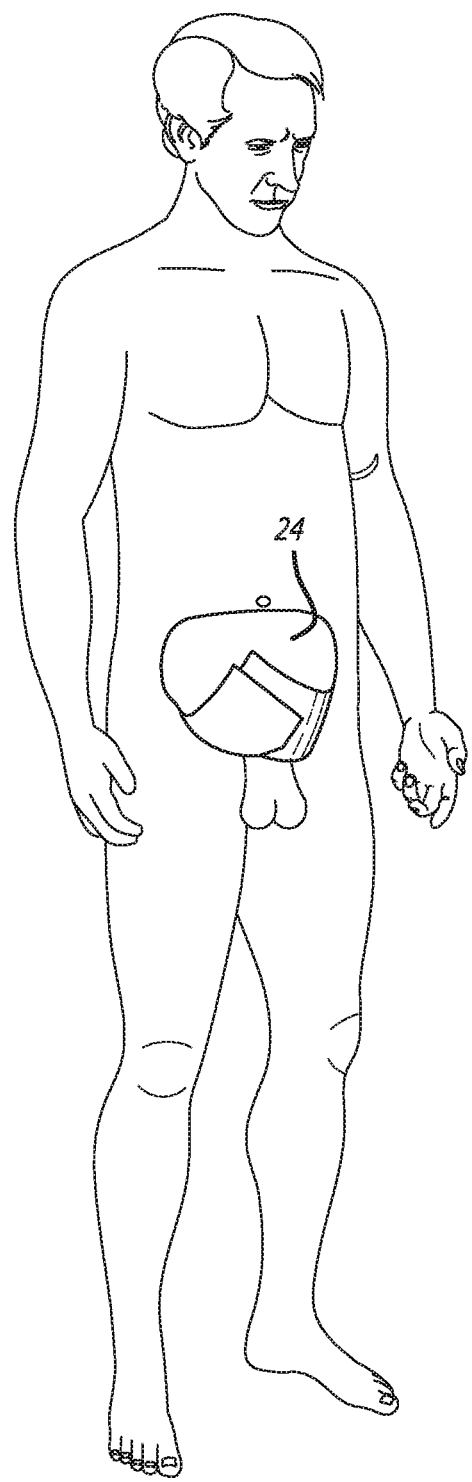
Figure 21:
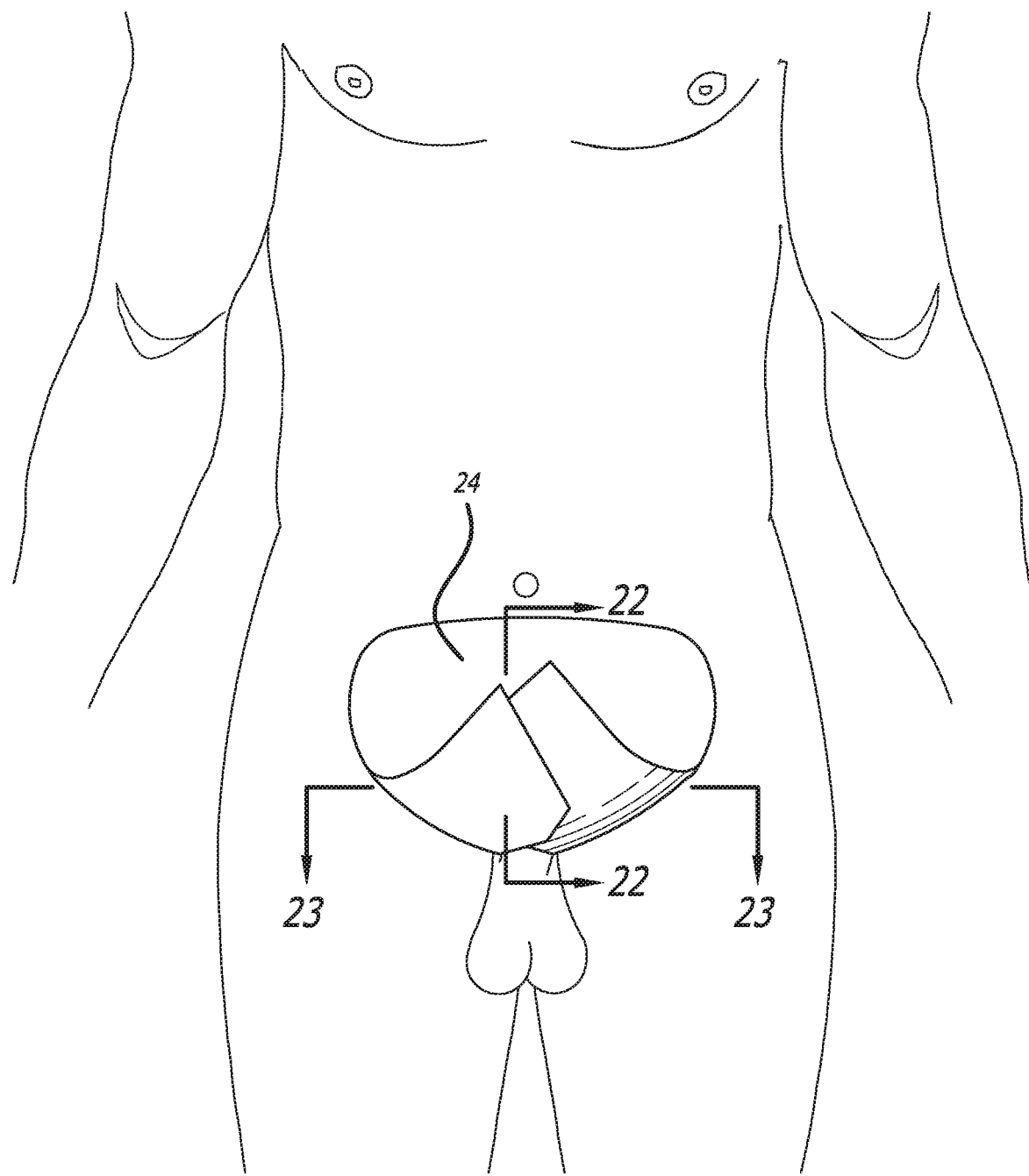
Figure 22:
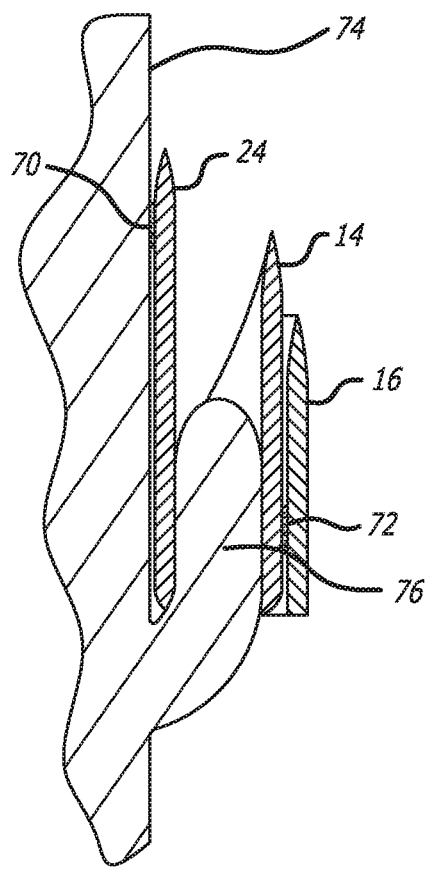
Figure 23:
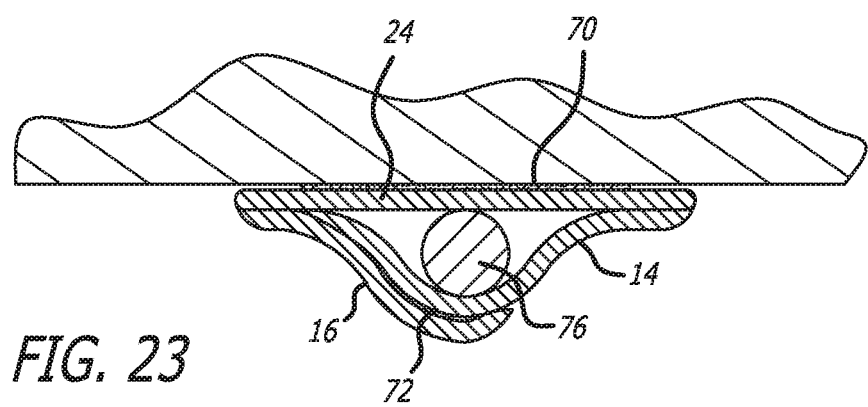

As shown in FIGS. 9-11, the urine trap 12 can be placed inside a diaper or underpants 90 of a patient 80 without the need to fully undress the patient. If the patient should have incontinence while wearing the urine trap, a caretaker can efficiently and quickly remove the soiled pad to be replaced by a new pad with minimal jostling or movement of the patient. That is, with the patient on his back, the caretaker may easily draw the front of the undergarment down to expose the trap and then lift the wings 16 and 14 so the soiled pad may be withdrawn for disposal, all without lifting or maneuvering the weight of the patient. The caretaker may then select a replacement pad and apply to be held in place by a larger adhesive strip 70 placed on the backside of the pad to secure the pad to the patient's waistband 92 of his undergarment such as his outer diaper, pants or underwear 90 to maintain the urine trap in position. Alternatively, a plurality of adhesive strips can be secured to the back side or front side of the urine trap to secure it to a gown or other more loose-fitting clothing.

The unique shape, configuration and positioning of the first and second wings have multiple benefits over the existing prior art. First, the wings minimize the amount of material needed to establish a secure and reliable pouch, and eliminate excess flaps that can catch on garments and inadvertently open the pouch. For example, the inner side edge 46 of the second wing 16 aligns with the base of the first wing 14 at the fold line 30 when the second wing 16 is folded over the first wing 14. Similarly, the inner side edge 34 of the first wing 14 aligns perfectly with the base of the second wing 16 at the fold line 52 when the first wing 14 is folded over the penis. The alignment of the inner edges against the opposite crease maximizes the volume of the pouch and eliminates excess wing material bunching up or contacting the penis. The novel shape aligns the edges of the wings to ends of the pouch itself, creating a perfectly formed and reliable pouch with no excess material. Second, cut-outs 36, 54 form a more comfortable opening through which the wearer's penis is secured, reducing chaffing and skin irritation. By eliminating all excess material, the user can wear the urine trap under street clothes as well without large, bulky bulges that can be created by traditional diapers. A taped border may extend along the wings from the respective creases to ensure that the edges mate more smoothly and prevent gaps that can cause leakage.

In an alternative embodiment as shown in FIGS. 14-23, the pouch can be applied and worn in a reverse manner. Advantages may be seen in this configuration depending on whether the user is prone or ambulatory. The adhesive strip may be secured to the user 80 in this embodiment, wear only a gown or other loose fitting clothing are worn and there is nothing else to which one can apply the adhesive strip.

Figure 24A:
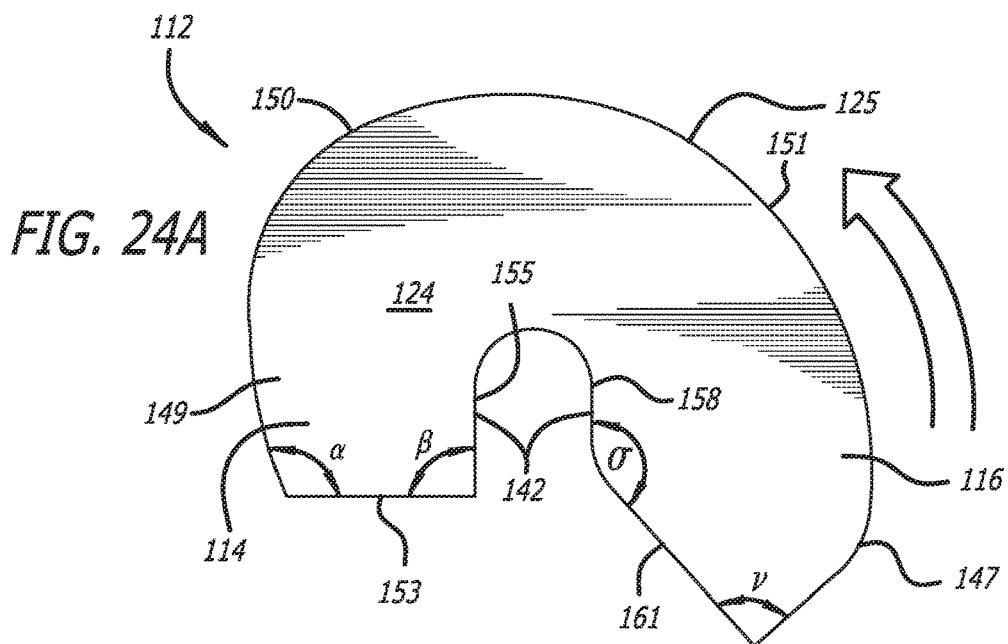
FIG. 24A is a planform view of an alternate embodiment of the pad of the present invention.
Figure 24B:
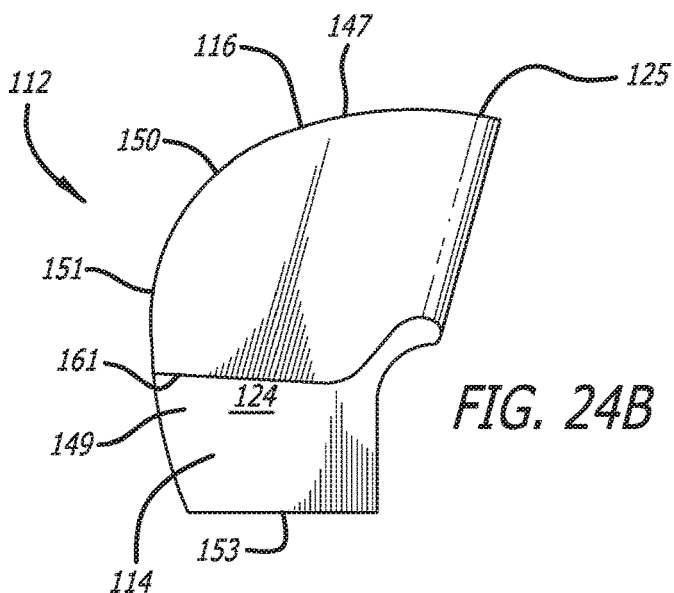
FIG. 24B is a top plan view of the pad shown in FIG. 24A but folded over on itself.
Figure 24C:
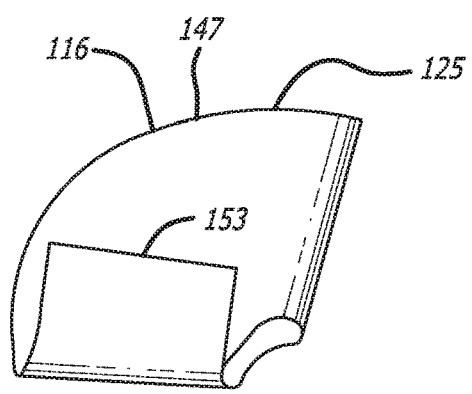
FIG. 24C is a top plan view similar to FIG. 24B but further folded over.
Figure 25:
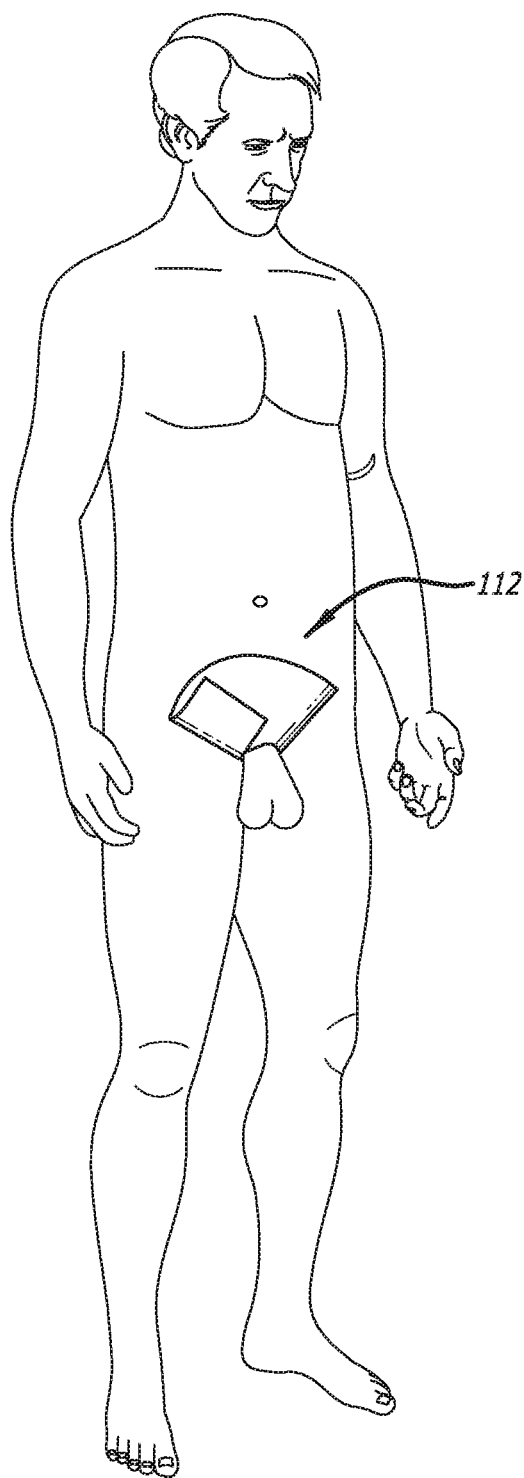
FIG. 25 is an elevated perspective view of the embodiment of FIG. 24 on a patient.

FIGS. 24 and 25 illustrate yet another embodiment 112 of a urinary pad that also includes an inner fluid transmissive layer, an absorbent layer, and a fluid impermeable layer cooperating to form a pad as previously discussed above. The pad 112 has a different shape that includes a main absorbent region 124 and first and second wings 114,116 defining a gap 142 between a portion of the first and second wings. The main absorbent region 124 is configured with a predetermined curved contour which in the preferred embodiment defines a substantially circular perimeter 125 extending from a rounded registration edge 150 in the upper left quadrant and curves around to the upper right quadrant to define the free edge 151 of the second wing 116 to then turn inwardly and downwardly to define and inwardly and downwardly angled edge 147. The first wing 114 is trapezoidal shaped with the outer side registration edge 149 and the distal edge 153 formed at an angle α that is approximately 105°, and the distal edge 153 and the inner edge 155 formed an included angle β that is substantially 90°. The second wing 116 includes an inner side edge 158, and a side edge 161, the inner side 158 substantially parallel to the inner edge 155 of the first wing 114, the outer side edge 147 and the side edge 161 forming an angle ν that is substantially 90° and the inner side edge 158 and the side edge 161 forming an angle θ that is substantially 135°, the second wing 116 extending distally beyond the distal edge 153 of the first wing 114.

The inner edges 155 and 158 of the wings cooperate to form an elongated gap 142 originating at a closed end to define an opening 156 and projects axially therefrom. Referring to FIG. 24B, the second wing 116 may thus be folded proximally and inwardly over the main absorbent region 124 sufficiently far to align the curved distal edge 151 with the curved registration edge 150 so those edges are somewhat congruent causing the absorbent layer of the periphery of the wing 116 to be protected from the patient's skin by the marginal edge of the main absorbent region. Thus, liquid distributed in the absorbent layer of the wing 116 will be physically blocked from direct contact with the patient's abdomen.

FIG. 25 illustrates one example of a patient wearing the embodiment of FIG. 24. The adhesive tape strips are substantially located as with the embodiment of FIGS. 14-23 although not shown for simplicity in FIGS. 24-25.

As will be appreciated by those skilled in the art, when laid flat as shown in FIG. 24, the wings 114 and 116 will be disposed in the same plane as the main absorbent region 124. Then, when placed on the abdomen of the patient, as shown in FIG. 25, the absorbent region 124 will typically lie directly on the abdomen with the penis projected through the opening 156 so the wing 116 may be raised from the distal outer edge 151 to fold over the main region 124 so that the registration edges 147 and 150 are aligned in somewhat congruent fashion, as shown in FIG. 25. The adhesive tape strip on the impermeable side of the wing 147 will thus be exposed. Then, the distal end of the first wing 114 may be folded proximally and laterally inwardly to a position overlying the wing 116 to cooperate therewith to form a double layer of absorbent material over the penis as it extends through the opening 156 to overlie the main region. In this arrangement, the penis will remain comfortably projecting through the open opening 156 but trapped in the trap created between the respective wings 114 and 116 and main absorbent region 124 to thereby contain and absorb any urine released.

As shown, the first wing 114 is formed with an area at least 20% as great as the main absorbent region 124. In practice, we prefer to configure the second wing 116 with at least 85% of the area of the main absorbent region and preferably 90% as shown. In the preferred embodiment, we configure the absorbent region with an area of 130 square inches and the wing 116 substantially the same or slightly less.

In practice, we have constructed the registration edges 150 and distal edge 151 with a continuous, common radius of curvature to thus induce the care giver to align these edges when dressing the patient. In other embodiments, such edges may be formed with other configurations of curved registration edges to induce registration. In practice we form these edges with a radius of curvature of 12 inches but understand that, depending on the patient, a radius of curvature of between 6 and 14 inches will suffice.

Figure 26A:
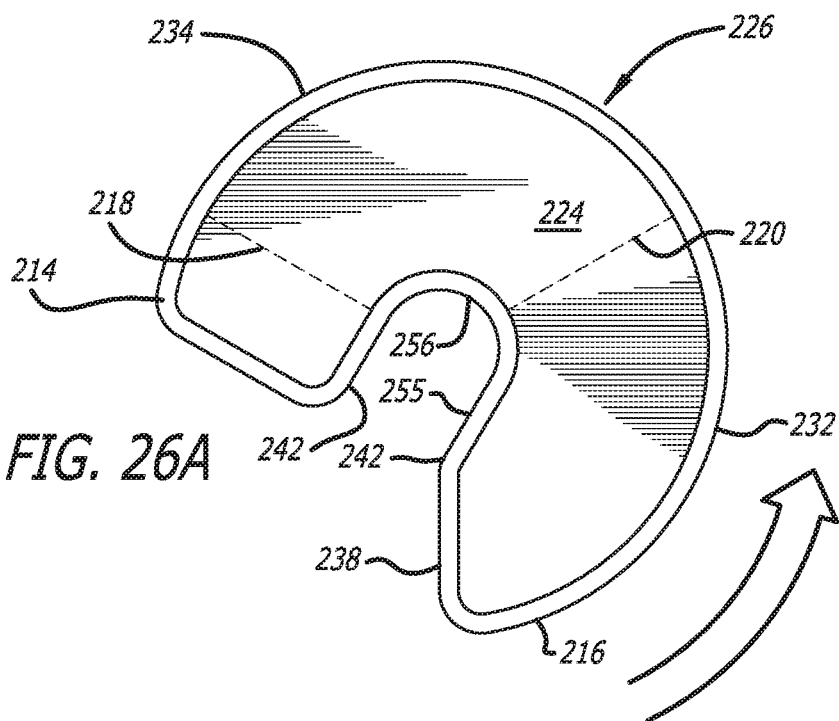
FIG. 26A is a top plan view of a further embodiment of the pad of the present invention.
Figure 26B:
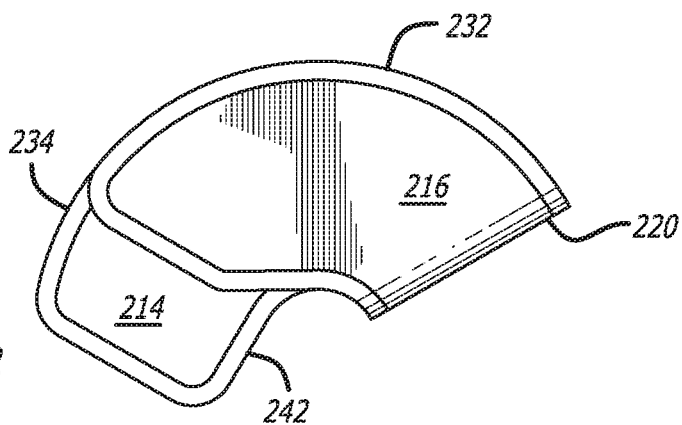
FIG. 26B is a plan view similar to FIG. 26A but folded over.
Figure 26C:
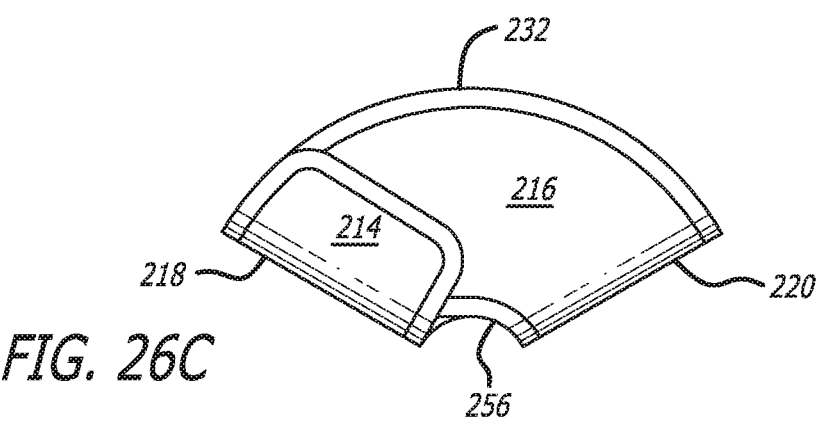
FIG. 26C is a view similar to FIG. 26B but further folded over.

Referring to FIGS. 26A-26C, in a further embodiment of the trap of the present invention, we incorporate a pad with a rounded peripheral edge to define a sector of a circle of approximately 300 degrees. The pad includes a central main absorbent section 224, a first wing 214 and a second wing 216, the wings being foldable along respective imaginary fold lines 218 and 220 to fold the wing 216 over on the main absorbent section 224. In this construction, for an adult male, we selected a radius of eight inches for the outside periphery 226 of the pad. It should be understood that a radius of between 6 inches and 14 inches will also suffice for different sizes of the pads of the present invention.

We have discovered that the area of the second wing should be at least 50% of the area of the main region and preferably about 90% to 100% of that area to create an effective trap. In one preferred embodiment we form the main region with an area of about 130 square inches and the second wing with about the same area to provide maximum absorption for minimum bulk.

In practice it will be appreciated that the subject pad is formed with a central U-shaped opening 255 by means of laterally spaced-apart edges 242 of the respective wings 214 and 216 to thus provide an opening for access of the patient's penis to be positioned in the opening 256 when the wings are folded over the main absorbent region 224.

It will be appreciated that when the second wing 216 is folded on the fold line 220, the circular peripheral, distal edge 232 thereof will be disposed in overlying relationship in proximity with the registration edge 234 of the main region, to dispose the terminal edge 238 generally along the fold line 218. This then places the wing 216 in covering relationship over the patient's penis as projected through the opening 256 to overlie the main absorbent region 224 to thus be disposed in a favorable location so the first wing 214 may be folded along the imaginary line 218 to overlie the edge of the wing 216 and, to be held in position by the patient's undergarment or adhesive tape attached to one or the other of the wings.

From the foregoing it will be apparent to those of skill in the art that with the construction of the pad of the present invention, the imaginary fold lines 218 and 220 are merely markers for convenience of explanation indicating where in may be desirable to make a fold. In some embodiments, the fold lines 218 and 220 are marked by indicia or other markers to help guide the caretaker. In practice, however, we have found that with the particular shape of the pads described hereinabove, the desirable fold lines are intuitive to the caretaker so that the folds may be made to position the wings in a somewhat conical configuration cooperating with the main region 224 for entrapping the penis within the opening 256 to maximize the comfort of the patient and minimize the opportunity for leakage stemming from any openings which might otherwise be left even with the trap closed. We formed the opening to remain open and not press on the penis.

By forming the distal edge of the second wing with a curve of approximating the shape of that of the periphery of the main absorbent region at the registration edge, as in this case, the same radius of curvature, the care taker is induced to substantially align those edges when forming the trap so as to leave no portion of the absorbent layer of the first wing exposed to the patient's skin to thus provide and barrier against urine making direct contact with the skin.

As will be appreciated by those of skill, the pads of the present invention are relatively small, with a high capacity for moisture absorption, and configured to form an envelope around the penis so that urine projected even by stream from the penis will be captured within the trap to escape therefrom and consequent contact with the patient's abdomen and consequent irritation to the skin. Additionally, it will be appreciated that the pads of the present invention serve to encapsulate the penis and maintain it isolated from the patient's anal area to thus protect against migration of feces and the like which may otherwise exist in the anal area and be conveyed to the patient's abdomen.

The trap is convenient to replace in the patient's undergarment, provides maximum absorption and highly effective protection with a minimum of bulk and cost of manufacture, as well as reducing the bulk of waste on disposal.

The foregoing description is intended to be illustrative and not exclusive. That is, there are many variations and modifications that can be made to the foregoing descriptions and preferred embodiments that would be readily apparent to one of ordinary skill in the art, and the present invention is intended to include all such modifications and variations. Such modifications may include choice of materials, overall dimensions of the embodiment, etc. Accordingly, the scope of the present invention should not be limited to any specific embodiment, illustration, or description herein, but rather the scope of the invention should be determined by the appended claims using the plain and ordinary meaning of the words used therein.

We claim:

1. A urine trap for a male patient, comprising:
    a pad having a fluid absorbent layer on a first surface and a fluid impermeable layer on an opposite surface, the pad further comprising:
    a first wing defined by a first fold line, an outer edge, an inner edge, and a lateral edge;
    a second wing defined by a second fold line, an outer edge, an inner edge, and a lateral edge substantially parallel to the second fold line; and
    a main absorbent region defined by the first fold line, the second fold line, an outer edge having a first radius, and an inner edge having a second radius; and
    the outer edge of the first wing defining a first arc that coincides with the outer edge of the main absorbent region and a portion of the inner edge of the first wing defining a second arc that coincides with a portion of the inner edge of the main absorbent region;
    the lateral edge of the first wing coincides with the second fold line; and
    the outer edge of the second wing defining a third arc that coincides with a portion of the outer edge of the main absorbent region and a portion of the outer edge of the first wing;
    whereby the main absorbent region, the first wing cooperate, and the second wing cooperate to form a conical compartment.

2. The urine trap of claim 1, further comprising an adhesive strip on the first surface at the main absorbent region.

3. The urine trap of claim 1, wherein the first arc is circular.

4. The urine trap of claim 1, wherein the second arc is circular.

5. The urine trap of claim 1, wherein the outer edge of the first wing, the outer edge of the main absorbent region, and the outer edge of the second wing define a circular arc of approximately three hundred degrees (300°).

6. The urine trap of claim 5, wherein a radius of the circular arc is eight inches.

7. The urine trap of claim 1, wherein the inner surface of the first wing, the inner surface of the main absorbent region, and the inner surface of the second wing defines a U-shaped periphery.

8. The urine trap of claim 1, where an area of the second wing is equal to an area of the main absorbent region.

* * * * *